US012611175B2

(12) United States Patent
Miyachi et al.

(10) Patent No.: US 12,611,175 B2
(45) Date of Patent: Apr. 28, 2026

(54) ULTRASOUND DIAGNOSTIC APPARATUS

(71) Applicant: FUJIFILM Corporation, Tokyo (JP)

(72) Inventors: Yukiya Miyachi, Ashigarakami-gun (JP); Kaku Irisawa, Ashigarakami-gun (JP); Keiji Tsubota, Ashigarakami-gun (JP); Tomoki Inoue, Ashigarakami-gun (JP); Katsuya Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 550 days.

(21) Appl. No.: 16/572,020

(22) Filed: Sep. 16, 2019

(65) Prior Publication Data

US 2020/0008782 A1    Jan. 9, 2020

Related U.S. Application Data

(63) Continuation of application No. PCT/JP2018/005394, filed on Feb. 16, 2018.

(30) Foreign Application Priority Data

Mar. 29, 2017    (JP) ................................. 2017-065095

(51) Int. Cl.
   *A61B 8/00*      (2006.01)
   *A61B 5/00*      (2006.01)

(52) U.S. Cl.
   CPC .......... *A61B 8/4444* (2013.01); *A61B 5/0095* (2013.01); *A61B 8/463* (2013.01);
        (Continued)

(58) Field of Classification Search
   CPC ..... A61B 8/4444; A61B 5/0095; A61B 8/463; A61B 8/5246; A61B 8/4272; A61B 8/4483
   See application file for complete search history.

(56) References Cited

U.S. PATENT DOCUMENTS

| | | | | |
|---|---|---|---|---|
| 5,957,846 A | * | 9/1999 | Chiang ................. | A61B 8/463 |
| | | | | 600/447 |
| 2004/0116813 A1 | * | 6/2004 | Selzer ................ | A61B 5/02007 |
| | | | | 600/467 |

(Continued)

FOREIGN PATENT DOCUMENTS

| | | |
|---|---|---|
| CN | 104337500 A | 2/2015 |
| CN | 104902823 A | 9/2015 |

(Continued)

OTHER PUBLICATIONS

Extended European Search Report, dated Mar. 16, 2020, for European Application No. 18777665.3.

(Continued)

*Primary Examiner* — Keith M Raymond
*Assistant Examiner* — Adam D. Kolkin
(74) *Attorney, Agent, or Firm* — Birch, Stewart, Kolasch & Birch, LLP

(57) ABSTRACT

Provided is an ultrasound diagnostic apparatus capable of synchronizing emission of light from a light source device emitting light for generating a photoacoustic wave and reception in an ultrasound probe with high accuracy. The ultrasound diagnostic apparatus includes a sub-controller that has a synchronization signal generation unit and controls an ultrasound probe based on a first synchronization signal generated by the synchronization signal generation unit, an image generation unit that generates an ultrasound image based on a signal detected by the ultrasound probe, and a connector that has a synchronization signal line for transmitting a second synchronization signal generated in the synchronization signal generation unit and outputs the second synchronization signal to the outside through the synchronization signal line. The connector is configured such that a photoacoustic wave light source unit emitting (Continued)

ULTRASONIC WAVE
TRANSMISSION TIMING SIGNAL

PHOTOACOUSTIC WAVE
TRANSMISSION TIMING SIGNAL

ULTRASONIC WAVE
RECEPTION TIMING SIGNAL

ULTRASONIC WAVE TRANSMISSION

PHOTOACOUSTIC WAVE TRANSMISSION

ULTRASONIC WAVE RECEPTION light incident on a puncture needle having a photoacoustic wave generation unit is connectable.

11 Claims, 13 Drawing Sheets

(52) U.S. Cl.
CPC .......... *A61B 8/5246* (2013.01); *A61B 8/4272* (2013.01); *A61B 8/4483* (2013.01)

(56) References Cited

U.S. PATENT DOCUMENTS

| | | | |
|---|---|---|---|
| 2004/0131299 A1 | 7/2004 | Adoram et al. | |
| 2009/0088821 A1* | 4/2009 | Abrahamson | H04J 3/0667 |
| | | | 607/60 |
| 2013/0141557 A1* | 6/2013 | Kawata | A61B 1/045 |
| | | | 348/65 |
| 2014/0187902 A1 | 7/2014 | Sato et al. | |
| 2015/0038845 A1* | 2/2015 | Agano | A61B 5/0095 |
| | | | 600/407 |
| 2015/0182124 A1* | 7/2015 | Abe | A61B 5/0095 |
| | | | 600/407 |
| 2015/0297092 A1 | 10/2015 | Irisawa | |
| 2016/0136689 A1 | 5/2016 | Murakoshi | |
| 2016/0206284 A1* | 7/2016 | Lee | A61B 8/4438 |
| 2016/0303354 A1* | 10/2016 | Burkett | A61B 5/0215 |
| 2017/0014053 A1* | 1/2017 | Moehring | A61B 8/12 |
| 2017/0112386 A1 | 4/2017 | Irisawa | |
| 2018/0078235 A1 | 3/2018 | Irisawa | |

FOREIGN PATENT DOCUMENTS

| | | | | |
|---|---|---|---|---|
| CN | 105796127 | A | | 7/2016 |
| CN | 106361290 | A | | 2/2017 |
| CN | 106470614 | A | | 3/2017 |
| JP | 2015231582 | A | * | 12/2015 |
| JP | 2016-64010 | A | | 4/2016 |
| KR | 10-2016-0114012 | A | | 10/2016 |
| WO | WO 2014/017044 | A1 | | 1/2014 |
| WO | WO 2016/0061 | A1 | | 1/2016 |
| WO | WO 2017/002338 | A1 | | 1/2017 |

OTHER PUBLICATIONS

Haisch et al., "Quantitative Analysis with the Optoacoustic/ Ultrasound System OPUS," Proceedings of SPIE (International Society for Optical Engineering), vol. 7177, San Jose, California, USA, Mar. 4, 2009 (Feb. 12, 2009), 10 pages, XP055673864.
International Preliminary Report on Patentability and Written Opinion of the International Searching Authority, dated Oct. 10, 2019, for International Application No. PCT/JP2018/005394, with a Written Opinion translation.
International Search Report, dated May 1, 2018 for International Application No. PCT/JP2018/005394, with an English translation.
Chinese Office Action and Search Report for Chinese Application No. 201880021555.0, dated Aug. 13, 2021, with an English translation.
Chinese Office Action and Search Report for Chinese Application No. 201880021555.0, dated Jan. 7, 2022, with an English translation.
Chinese Office Action for Chinese Application No. 201880021555.0, dated May 5, 2022, with English translation.
Chinese Office Action for Chinese Application No. 201880021555.0, dated Dec. 28, 2022, with an English translation.
Chinese Office Action and Search Report for corresponding Chinese Application No. 202310383146.8, dated Jun. 17, 2025, with partial English translation.

* cited by examiner

ULTRASONIC WAVE
TRANSMISSION TIMING SIGNAL

ECG SIGNAL DETECTION
TIMING SIGNAL

ULTRASONIC WAVE
RECEPTION TIMING SIGNAL

ULTRASONIC WAVE
TRANSMISSION

ECG SIGNAL DETECTION

ULTRASONIC WAVE RECEPTION

ULTRASONIC WAVE
TRANSMISSION TIMING SIGNAL

PHOTOACOUSTIC WAVE
TRANSMISSION TIMING SIGNAL

ULTRASONIC WAVE RECEPTION
TIMING SIGNAL

ULTRASONIC WAVE
TRANSMISSION

PHOTOACOUSTIC WAVE
TRANSMISSION

ULTRASONIC WAVE RECEPTION

ULTRASONIC WAVE
TRANSMISSION TIMING SIGNAL

ULTRASONIC WAVE
RECEPTION TIMING SIGNAL

CW DEDICATED TRANSMISSION
TIMING SIGNAL

CW DEDICATED RECEPTION
TIMING SIGNAL

ULTRASONIC WAVE TRANSMISSION

ULTRASONIC WAVE RECEPTION

CW DEDICATED TRANSMISSION SIGNAL

CW DEDICATED RECEPTION SIGNAL

ULTRASOUND DIAGNOSTIC APPARATUS

CROSS-REFERENCE TO RELATED APPLICATIONS

This application is a Continuation of PCT International Application No. PCT/JP2018/005394 filed on Feb. 16, 2018, which claims priority under 35 U.S.C § 119(a) to Japanese Patent Application No. 2017-065095 filed on Mar. 29, 2017. Each of the above application(s) is hereby expressly incorporated by reference, in its entirety, into the present application.

BACKGROUND OF THE INVENTION

1. Field of the Invention

The present invention relates to an ultrasound diagnostic apparatus to which a light source device emitting light for generating a photoacoustic wave is connectable.

2. Description of the Related Art

As one kind of image inspection method that can noninvasively inspect a state inside a living body, an ultrasonography method is known. In ultrasonography, an ultrasound probe that can transmit and receive an ultrasonic wave is used. In a case where an ultrasonic wave is transmitted from the ultrasound probe to a subject (living body), the ultrasonic wave advances through the inside of the living body and is reflected from a tissue interface. The reflected ultrasonic wave is received by the ultrasound probe, and a distance is calculated based on a time until the reflected ultrasonic wave returns to the ultrasound probe, whereby it is possible to image the status of the inside.

Furthermore, photoacoustic imaging using a puncture needle provided with a photoacoustic wave generation unit absorbing light and generating a photoacoustic wave near a distal end has been suggested. In the puncture needle, an optical fiber is provided to the distal end of the puncture needle, and the photoacoustic wave generation unit is irradiated with light guided by the optical fiber. A photoacoustic wave generated in the photoacoustic wave generation unit is detected by the ultrasound probe, and a photoacoustic image is generated based on a detection signal. In the photoacoustic image, a portion of the photoacoustic wave generation unit appears as a bright spot, making it possible to confirm the distal end position of the puncture needle using the photoacoustic image.

In JP2015-231582A, a system that connects a light source device making light incident on the above-described puncture needle to an ultrasound diagnostic apparatus for ultrasonography and can acquire both of an ultrasound image and a photoacoustic image has been suggested.

SUMMARY OF THE INVENTION

Here, in a case of confirming the distal end position of the puncture needle using the photoacoustic image as described above, there is a need to display the distal end position of the puncture needle with distance accuracy of equal to or less than 0.1 mm. The reason is that ultrasonic measurement is generally performed with accuracy of 0.1 mm. Furthermore, the reason is that the size of the puncture needle is about 0.3 mm to 1.2 mm, and for example, in a case where the puncture needle of 0.4 mm is used, accuracy of about 25% of the size of the puncture needle, that is, about 0.1 mm is needed.

The photoacoustic image is detected in a case where the photoacoustic wave generation unit absorbs light emitted from the light source device to generate the photoacoustic wave and the photoacoustic wave is received by the ultrasound probe as described above. For this reason, there is a need to synchronize emission of light from the light source device and reception in the ultrasound probe.

In order to implement the distance accuracy of equal to or less than 0.1 mm, a synchronization signal for synchronizing emission of light from the light source device and reception in the ultrasound probe should not be deviated by a desired time or more. Specifically, for example, in a case where a sonic speed of the photoacoustic wave is 1540 m/s, the synchronization signal should not be deviated by 0.1 mm/1540 m/s=0.06 µs or more.

However, as described in JP2015-231582A, in a case where the light source device and the ultrasound diagnostic apparatus are connected by a universal serial bus (USB) connector, since a communication speed is limited, the synchronization signal cannot be transmitted with time accuracy of equal to or less than 0.06 µs. Specifically, for example, since a minimum unit of one packet is 125 µs even in a high-speed USB, such as USB 2.0 and USB 3.1, the synchronization signal cannot be transmitted with higher time accuracy. In a case where the synchronization signal is deviated by 125 µs, since the distance is deviated by 193 mm, an accurate distal end position of the puncture needle cannot be ascertained The invention has been accomplished in consideration of the above-described situation, and an object of the invention is to provide an ultrasound diagnostic apparatus capable of synchronizing emission of light from a light source device and reception in an ultrasound probe with high accuracy.

An ultrasound diagnostic apparatus of the invention comprises a controller that has a synchronization signal generation unit generating a first synchronization signal for controlling transmission and reception of an ultrasonic wave in an ultrasound probe, and controls the ultrasound probe based on the first synchronization signal, an ultrasound image generation unit that generates an ultrasound image based on a signal detected by the ultrasound probe, and a connector that has a synchronization signal line transmitting a second synchronization signal generated in the synchronization signal generation unit or a signal generated based on the second synchronization signal and outputs the second synchronization signal or the signal generated based on the second synchronization signal to the outside through the synchronization signal line. The connector is configured such that a light source device emitting light incident on an insertion object having a photoacoustic wave generation unit absorbing the light and generating a photoacoustic wave is connectable.

In the ultrasound diagnostic apparatus of the invention described above, the light source device may emit the light based on the second synchronization signal.

In the ultrasound diagnostic apparatus of the invention described above, the connector may be configured such that another device different from the light source device is connectable.

In the ultrasound diagnostic apparatus of the invention described above, identification information for identifying the another device may be stored in the another device, and the controller may acquire the identification information through the connector and control the output of the second synchronization signal according to the acquired identification information.

In the ultrasound diagnostic apparatus of the invention described above, the connector is configured such that an electrocardiograph, a phonocardiograph, or a probe for continuous wave Doppler measurement is connectable.

In the ultrasound diagnostic apparatus of the invention described above, the synchronization signal generation unit may have a clock signal generation unit generating a clock signal, and the connector may have a clock signal line transmitting the clock signal and output the clock signal to the outside through the clock signal line.

In the ultrasound diagnostic apparatus of the invention described above, a processor constituting the ultrasound image generation unit may operate based on a clock signal different from the clock signal.

In the ultrasound diagnostic apparatus of the invention described above, the synchronization signal generation unit may generate the first synchronization signal and the second synchronization signal such that the light source device emits the light multiple times while a signal of one line is being detected by the ultrasound probe.

In the ultrasound diagnostic apparatus of the invention described above, the synchronization signal generation unit may generate the first synchronization signal and the second synchronization signal such that the light source device emits the light multiple times while a signal of one frame is being detected by the ultrasound probe.

The ultrasound diagnostic apparatus of the invention described above may be portable.

With the ultrasound diagnostic apparatus of the invention, the ultrasound probe is controlled based on the first synchronization signal generated by the synchronization signal generation unit, the connector having the synchronization signal line transmitting the second synchronization signal generated by the synchronization signal generation unit or the signal generated based on the second synchronization signal is provided, and the light source device emitting light, with which the photoacoustic wave generation unit is irradiated, is connectable to the connector, whereby it is possible to synchronize emission of light from the light source device and reception in the ultrasound probe with high accuracy.

BRIEF DESCRIPTION OF THE DRAWINGS

FIG. 1 is a block diagram showing the schematic configuration of an ultrasound diagnostic system using a first embodiment of an ultrasound diagnostic apparatus of the invention.

FIG. 2 is a block diagram showing the schematic configuration of the ultrasound diagnostic system using the first embodiment of the ultrasound diagnostic apparatus of the invention.

FIG. 9 is a block diagram showing the schematic configuration of an ultrasound diagnostic system using a second embodiment of an ultrasound diagnostic apparatus of the invention.

FIG. 10 is a block diagram showing the schematic configuration of an ultrasound diagnostic system using a second embodiment of an ultrasound diagnostic apparatus of the invention.

DESCRIPTION OF THE PREFERRED EMBODIMENTS

Figure 1:
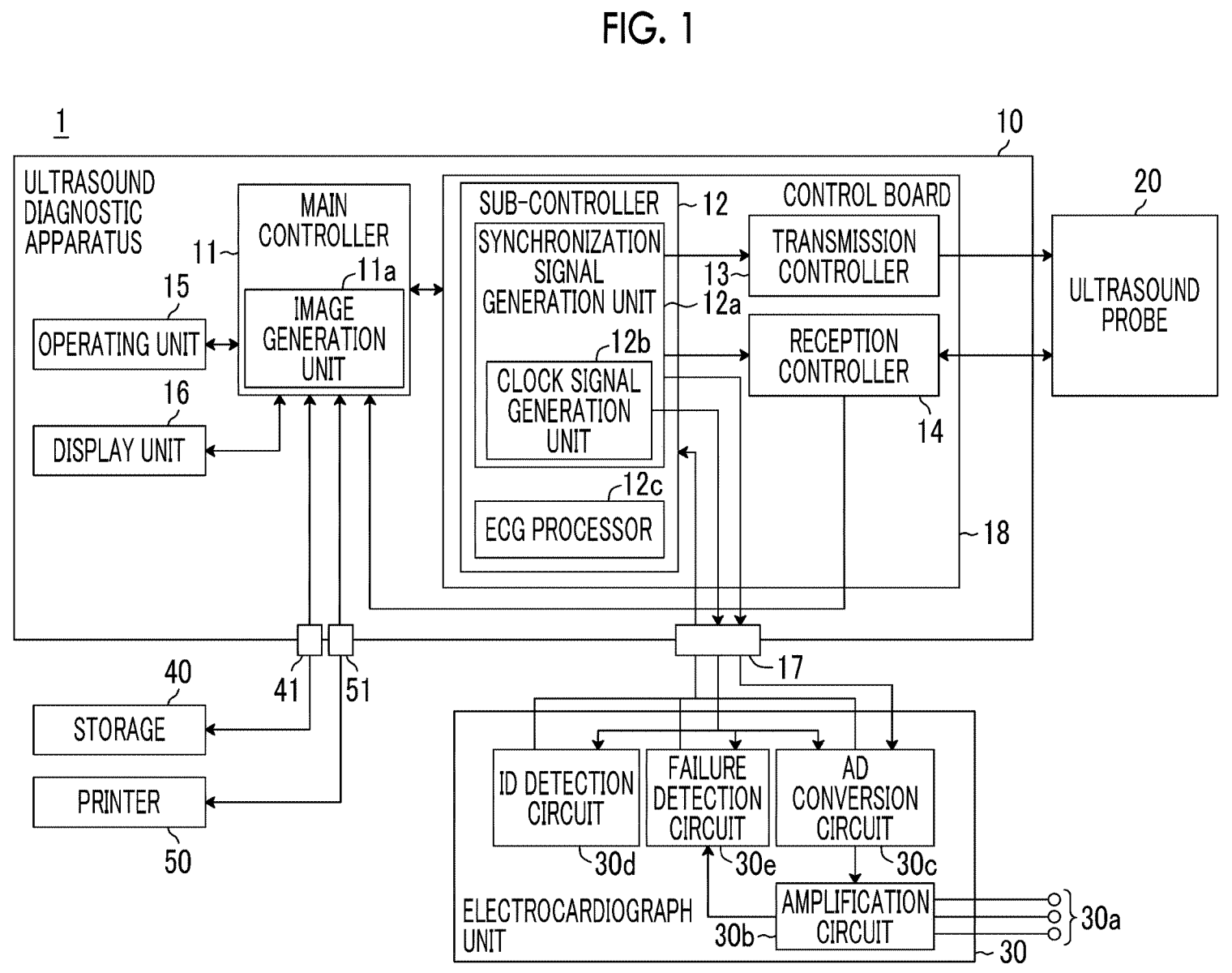
Figure 2:
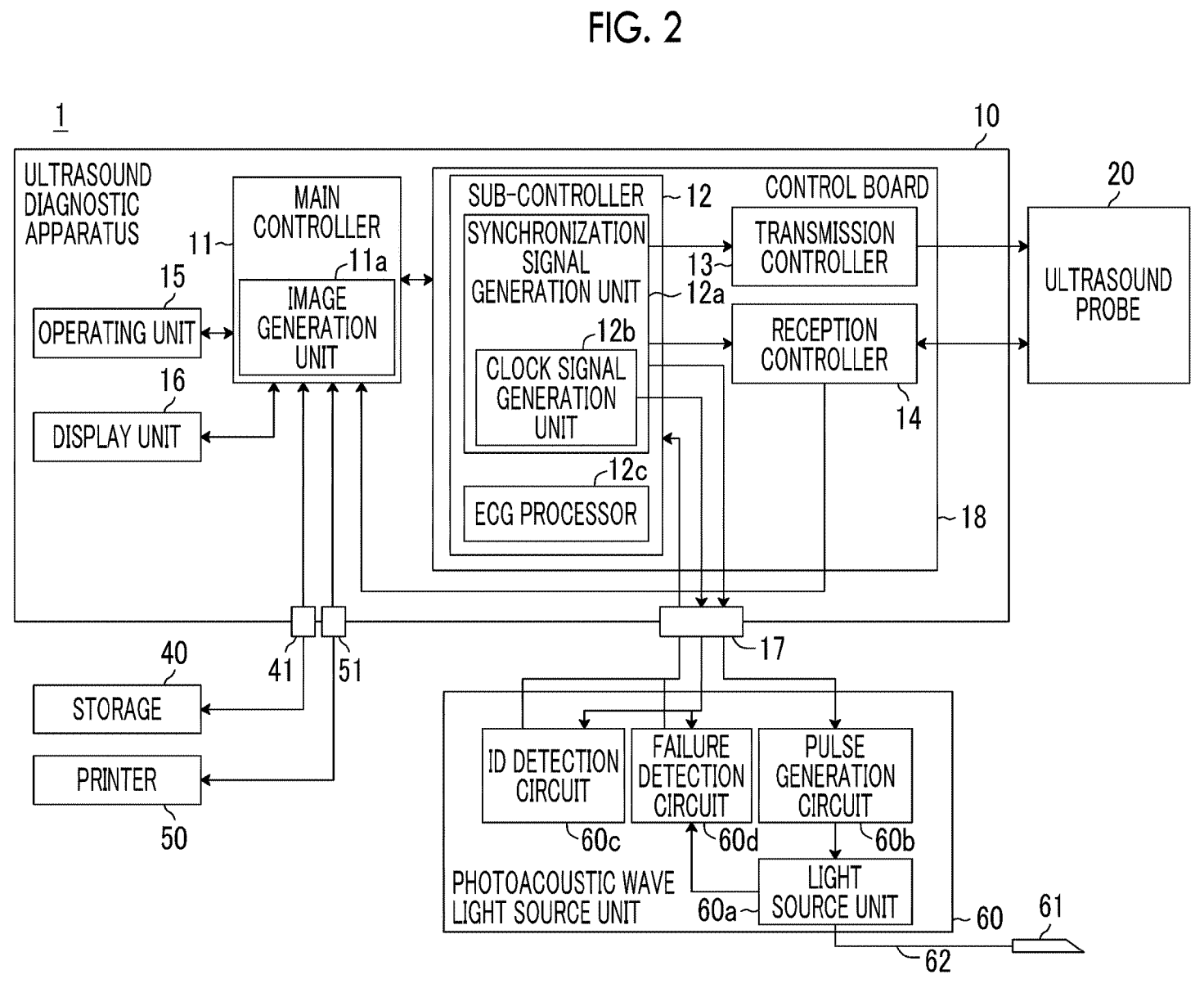
Figure 3:
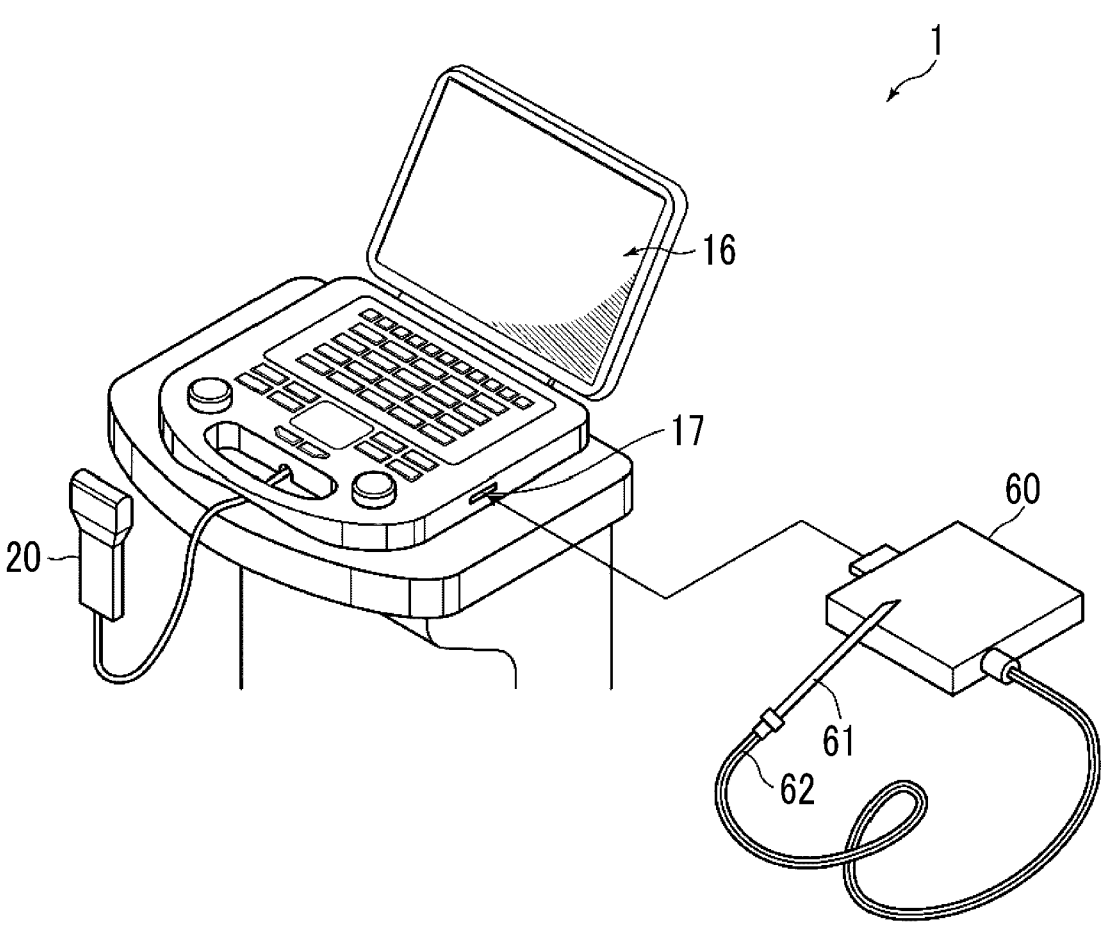
FIG. 3 is an appearance perspective view of the ultrasound diagnostic system using the first embodiment of the ultrasound diagnostic apparatus of the invention.

Hereinafter, an ultrasound diagnostic system using a first embodiment of an ultrasound diagnostic apparatus of the invention will be described in detail referring to the drawings. FIGS. 1 and 2 are block diagrams showing the schematic configuration of an ultrasound diagnostic system 1 of the embodiment. FIG. 3 is an appearance perspective view of the ultrasound diagnostic system 1 of the embodiment.

As shown in FIGS. 1 and 2, the ultrasound diagnostic system 1 of the embodiment comprises an ultrasound diagnostic apparatus 10, an ultrasound probe 20, an electrocardiograph unit 30, a photoacoustic wave light source unit 60, a storage 40, and a printer 50.

In the ultrasound diagnostic system 1 shown in FIG. 1, the electrocardiograph unit 30 (corresponding to an electrocardiograph of the invention) is connected to a connector 17 of the ultrasound diagnostic apparatus 10. As shown in FIG. 2, the connector 17 is configured such that the photoacoustic wave light source unit 60 (corresponding to a light source device of the invention) is also connectable. That is, the connector 17 of the ultrasound diagnostic apparatus 10 of the embodiment is configured such that both of the electrocardiograph unit 30 and the photoacoustic wave light source unit 60 are connectable, and one of these units is connected to the connector 17. The configuration of the connector 17 will be described below in detail.

FIG. 3 shows a state in which the photoacoustic wave light source unit 60 is connected to the connector 17 of the ultrasound diagnostic apparatus 10. As shown in FIG. 3, the ultrasound diagnostic apparatus 10 of the embodiment is configured portable and is configured such that a cable of the ultrasound probe 20 is connected to a bottom surface of the ultrasound diagnostic apparatus 10. The ultrasound diagnostic system 1 shown in FIG. 2 is the same as the ultrasound diagnostic system 1 shown in FIG. 1 except that, instead of the electrocardiograph unit 30 in the ultrasound diagnostic system 1 shown in FIG. 1, the photoacoustic wave light source unit 60 is connected to the connector 17.

First, the ultrasound diagnostic apparatus 10 in the ultrasound diagnostic system 1 of the embodiment will be described. The ultrasound diagnostic apparatus 10 comprises a main controller 11, a sub-controller 12 (corresponding to a controller of the invention), a transmission controller 13, a reception controller 14, an operating unit 15, a display unit 16, and the above-described connector 17. The sub-controller 12, the transmission controller 13, and the reception controller 14 are provided on a control board 18 separate from the main controller 11.

The main controller 11 controls the whole system, and comprises a central processing unit (CPU) and the like. The main controller 11 also comprises an image generation unit 11a (corresponding to an ultrasound image generation unit of the invention). The image generation unit 11a generates an ultrasound image and a photoacoustic image based on a detection signal detected by the ultrasound probe 20. Generation processing of the ultrasound image and the photoacoustic image includes, for example, image reconstruction, such as phasing addition, detection, logarithmic conversion, and the like.

The sub-controller 12 comprises a processor and the like, and controls transmission of an ultrasonic wave from the ultrasound probe 20 and reception of a reflected ultrasonic wave reflected from a subject with the transmission of the ultrasonic to the subject. Furthermore, the sub-controller 12 controls reception of an electrocardiogram (ECG) signal output from the electrocardiograph unit 30 and controls emission of light from the photoacoustic wave light source unit 60.

Specifically, the sub-controller 12 comprises a synchronization signal generation unit 12a and an ECG processor 12c. The synchronization signal generation unit 12a comprises a clock signal generation unit 12b.

The clock signal generation unit 12b generates a clock signal, and comprises a quartz crystal resonator and the like. The synchronization signal generation unit 12a comprises a phase locked loop (PLL) circuit and the like, and multiplies the clock signal generated in the clock signal generation unit 12b to generate a synchronization signal. A frequency of the clock signal can be set to, for example, 40 MHz, and a frequency of the synchronization signal can be set to, for example, 160 MHz.

The synchronization signal generated in the synchronization signal generation unit 12a is output to the transmission controller 13 and the reception controller 14. The transmission controller 13 controls a transmission timing of the ultrasonic wave from the ultrasound probe 20 based on the input synchronization signal. The reception controller 14 controls a reception timing of the reflected ultrasonic wave of the ultrasound probe 20 based on the input synchronization signal. In the embodiment, the synchronization signal that is input to the transmission controller 13 and the reception controller 14 corresponds to a first synchronization signal of the invention. The transmission controller 13 and the reception controller 14 comprise an electric circuit that performs transmission and reception control described above, and the like.

The synchronization signal generated in the synchronization signal generation unit 12a is output to the outside through the connector 17 and is input to the electrocardiograph unit 30 or the photoacoustic wave light source unit 60 connected to the connector 17. The electrocardiograph unit 30 detects the ECG signal based on the input synchronization signal. The photoacoustic wave light source unit 60 controls an emission timing of light for generating a photoacoustic wave based on the input synchronization signal.

In the embodiment, that synchronization signal that is input to the electrocardiograph unit 30 or the photoacoustic wave light source unit 60 corresponds to a second synchronization signal of the invention.

It is preferable that the processor of the main controller 11 having the image generation unit 11a is operated based on a clock signal different from the clock signal generated by the clock signal generation unit 12b of the sub-controller 12. In this way, the clock signal of the processor of the main controller 11 and the clock signal of the processor of the sub-controller 12 are different, whereby there is no need to synchronize the main controller 11 and the sub-controller 12, there is no need for a countermeasure against a circuitry delay or the like, and a simple configuration can be achieved. While the main controller 11 executes the generation processing of the ultrasound image and the photoacoustic image and storing the ultrasound image and the photoacoustic image to execute processing with no need for temporal synchronization with high accuracy, since various tasks are provided, the main controller 11 allocates the tasks with an operating system (OS) using a general-purpose CPU.

It should be noted that, in the control with the OS, a delay is likely to occur in a case where a load on the CPU increases, and the control with the OS is not suitable for synchronization with high accuracy. The sub-controller 12 needs for synchronization with high accuracy of transmission and reception control and the like. In the embodiment, the main controller 11 and the sub-controller 12 are independent. Accordingly, for example, even in a case where the load of the main controller 11 increases, since the sub-controller 12 performs digital control independently of the main controller 11, it is possible continuously perform control with high accuracy.

The ECG processor 12c receives the ECG signal detected based on the synchronization signal output from the synchronization signal generation unit 12a and outputs the received ECG signal to the main controller 11 along with the timing at which the synchronization signal is transmitted to the electrocardiograph unit 30. The main controller 11 makes the display unit 16 display the input ECG signal.

Figure 4:
FIG. 4 is a timing chart of an ECG detection mode.

FIG. 4 is a timing chart showing the synchronization signal that is output from the synchronization signal generation unit 12a, a transmission timing of an ultrasonic wave based on the synchronization signal, a detection timing of the ECG signal, and a reception timing of the ultrasonic wave. An ultrasonic wave transmission timing signal shown in FIG. 4 is a synchronization signal that is output from the synchronization signal generation unit 12a to the transmission controller 13, an ECG signal detection timing signal is a synchronization signal that is output from the synchronization signal generation unit 12a to the electrocardiograph unit 30, and an ultrasonic wave reception timing signal is a synchronization signal that is output from the synchronization signal generation unit 12a to the reception controller 14.

As shown in FIG. 4, the ultrasonic wave transmission timing signal, the ECG signal detection timing signal, and the ultrasonic wave reception timing signal are output at the same timing, and ultrasonic wave transmission and detection of the ECG signal are performed synchronously. The reception controller 14 starts reception of the reflected ultrasonic wave after a given delay time (for example, about 0.1 µs) from the timing at which the ultrasonic wave reception timing signal is received. Then, after the reflected ultrasonic wave is received in a given reception period, the reception controller 14 stops reception. The reception period can be set to a time (0.3 m×2/1540 m/s=0.39 ms; 1540 m/s is a sonic speed of an ultrasonic wave (10 MHz) to be transmitted)

corresponding to a depth of about 30 cm, for example, taking a reverberation signal into consideration as well. Then, the reception controller 14 outputs a detection signal of the reflected ultrasonic wave to the main controller 11 along with the timing at which the ultrasonic wave reception timing signal is received. The ultrasound image is generated by the image generation unit 11*a* of the main controller 11 based on the detection signal of the reflected ultrasonic wave. The main controller 11 makes the display unit 16 display the ultrasound image and an ECG waveform based on the ECG signal at the same timing.

Returning to FIG. 1, the operating unit 15 receives various operations of the user, and comprises a keyboard, operation buttons, and the like as shown in FIG. 3. The operating unit 15 of the embodiment receives ON and OFF operations of an ECG detection mode and ON and OFF operations of a photoacoustic image mode.

In a case where the ON operation of the ECG detection mode is received in the operating unit 15, the synchronization signal generation unit 12*a* outputs the ECG signal detection timing signal based on a control schedule set in advance. In a case where the ON operation of the photoacoustic image mode is received in the operating unit 15, the synchronization signal generation unit 12*a* outputs a photoacoustic wave transmission timing signal described below based on a control schedule set in advance.

The display unit 16 comprises a liquid crystal display or the like, and displays the ultrasound image and the photoacoustic image generated in the image generation unit 11*a*, and the ECG waveform based on the ECG signal output from the ECG processor 12*c*.

The ultrasound diagnostic apparatus 10 comprises USB connectors 41 and 51 different from the connector 17. For example, the storage 40 is connected to the USB connector 41, and for example, the printer 50 is connected to the USB connector 51.

Next, the electrocardiograph unit 30 will be described. The electrocardiograph unit 30 comprises an electrode group 30*a* that is mounted on the subject, an amplification circuit 30*b*, an AD conversion circuit 30*c*, an ID detection circuit 30*d*, and a failure detection circuit 30*e*.

The amplification circuit 30*b* amplifies the ECG signal detected by the electrode group 30*a*. The AD conversion circuit 30*c* converts the ECG signal amplified by the amplification circuit 30*b* to a digital signal and outputs the digital signal to the ultrasound diagnostic apparatus 10. The AD conversion circuit 30*c* operates in response to the ECG signal detection timing signal output from the synchronization signal generation unit 12*a* and outputs the ECG signal to the ECG processor 12*c*.

The ID detection circuit 30*d* comprises a memory that stores ID information (corresponding to identification information for identifying the device) of the electrocardiograph unit 30, a reading circuit that reads the ID information from the memory, and the like. The ID detection circuit 30*d* outputs the ID information to the sub-controller 12 of the ultrasound diagnostic apparatus 10 when the electrocardiograph unit 30 is connected to the connector 17 of the ultrasound diagnostic apparatus 10 or when the ultrasound diagnostic apparatus 10 is started after the connection of the electrocardiograph unit 30. As a method of detecting that the electrocardiograph unit 30 is connected to the ultrasound diagnostic apparatus 10, various kinds of known connection detection can be used. For example, an optical sensor, such as a photocoupler, may be provided or detection may be performed with a mechanical configuration.

The sub-controller 12 performs ECG detection only in a case where the ECG detection mode is selected in the operating unit 15 and the ID information of the electrocardiograph unit 30 is received. That is, the sub-controller 12 outputs the ECG signal detection timing signal from the synchronization signal generation unit 12*a*. Even though the ECG detection mode is selected in the operating unit 15, in a case where ID information different from the ID information of the electrocardiograph unit 30 is received, the sub-controller 12 does not output the ECG signal detection timing signal.

Specifically, for example, in a case where the photoacoustic wave light source unit 60, instead of the electrocardiograph unit 30, is erroneously connected to the connector 17, since the ID information of the electrocardiograph unit 30 is not received, the sub-controller 12 does not output the ECG signal detection timing signal. With this, it is possible to restrain failure in the photoacoustic wave light source unit 60 and erroneous emission of light from the photoacoustic wave light source unit 60. In a case where the ECG detection mode is selected in the operating unit 15, and in a case where a device other than the electrocardiograph unit 30 is connected to the connector 17, the sub-controller 12 outputs the effect to the main controller 11, and the main controller 11 makes the display unit 16 display a warning message or the like.

The failure detection circuit 30*e* confirms whether or not there is failure in the electrocardiograph unit 30 when the electrocardiograph unit 30 is connected to the connector 17 of the ultrasound diagnostic apparatus 10, when the ultrasound diagnostic apparatus 10 is started after the connection of the electrocardiograph unit 30, or when the electrocardiograph unit 30 operates. As detection of failure in the electrocardiograph unit 30, for example, an abnormality of output of the amplification circuit 30*b* is detected. In a case where failure is detected by the failure detection circuit 30*e*, a detection signal is output to the main controller 11 through the sub-controller 12 of the ultrasound diagnostic apparatus 10, and the main controller 11 makes the display unit 16 displays the effect that failure is detected.

The AD conversion circuit 30*c*, the ID detection circuit 30*d*, and the failure detection circuit 30*e* in the electrocardiograph unit 30 are subjected to digital control based on the clock signal generated in the clock signal generation unit 12*b* of the ultrasound diagnostic apparatus 10. In this way, the clock signal generation unit 12*b* of the ultrasound diagnostic apparatus 10 is used, whereby there is no need provide a clock signal generation unit in the electrocardiograph unit 30, and it is possible to achieve reduction in size.

Next, the photoacoustic wave light source unit 60 will be described. As shown in FIG. 2, the photoacoustic wave light source unit 60 comprises a light source unit 60*a*, a pulse generation circuit 60*b*, an ID detection circuit 60*c*, and a failure detection circuit 60*d*.

The light source unit 60*a* emits light for generating a photoacoustic wave, and comprises a laser diode (LD), a light emitting diode (LED), or the like. The pulse generation circuit 60*b* generates a pulse signal based on the synchronization signal output from the synchronization signal generation unit 12*a*. The light source unit 60*a* emits pulsed light in response to the pulse signal output from the pulse generation circuit 60*b*.

One end of an optical cable 62 comprising an optical fiber is connected to the photoacoustic wave light source unit 60, and a puncture needle 61 is connected to the other end of the optical cable 62.

Figure 5:
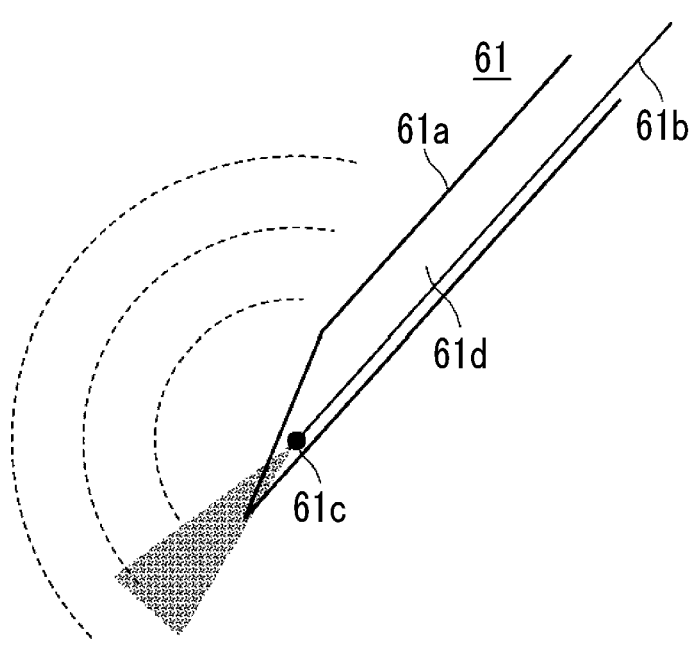
FIG. 5 is a cross-sectional view including a center axis extending in a lengthwise direction of a puncture needle.

The puncture needle 61 is an embodiment of an insertion object of the invention, and is a needle that is punctured into the subject. FIG. 5 is a cross-sectional view including a central axis extending in a lengthwise direction of the puncture needle 61. The puncture needle 61 has an opening at a distal end formed at an acute angle, and includes a puncture needle body 61*a* formed in a hollow shape, an optical fiber 61*b* that guides light emitted from the photoacoustic wave light source unit 60 to the vicinity of the opening of the puncture needle 61, and a photoacoustic wave generation unit 61*c* that absorbs light emitted from the optical fiber 61*b* to generate a photoacoustic wave.

The optical fiber 61*b* and the photoacoustic wave generation unit 61*c* are arranged in a hollow portion 61*d* of the puncture needle body 61*a*. The optical fiber 61*b* is connected to the optical fiber in the optical cable 62, for example, through an optical connector provided at a base end portion of the puncture needle 61.

The photoacoustic wave generation unit 61*c* is provided on a light emission side of the optical fiber 61*b*, and is provided in the vicinity of the distal end of the puncture needle 61 and in an inner wall of the puncture needle body 61*a*. The photoacoustic wave generation unit 61*c* absorbs light emitted from the optical fiber 61*b* to generate a photoacoustic wave. The photoacoustic wave generation unit 61*c* is formed of, for example, epoxy resin mixed with a black pigment, polyurethane resin, fluororesin, silicon rubber, or the like. In FIG. 5, although the photoacoustic wave generation unit 61*c* is drawn to be greater than the optical fiber 61*b*, the invention is not limited thereto, and the photoacoustic wave generation unit 61*c* may have a size similar to the diameter of the optical fiber 61*b*.

The photoacoustic wave generation unit 61*c* is limited to that described above, and a metal film or a film of an oxide having light absorbency with respect to the wavelength of light may be used as the photoacoustic wave generation unit. For example, as the photoacoustic wave generation unit 61*c*, a film of an oxide, such as an iron oxide, a chromium oxide, or a manganese oxide, having high light absorbency with respect to the wavelength of light can be used. Alternatively, a metal film, such as titanium (Ti) or platinum (Pt) having lower light absorbency but higher biocompatibility than an oxide may be used as the photoacoustic wave generation unit 61*c*. The position where the photoacoustic wave generation unit 61*c* is provided is not limited to the inner wall of the puncture needle body 61*a*. For example, the metal film or the film of the oxide as the photoacoustic wave generation unit 61*c* may be formed on a light emission end of the optical fiber 61*b*, for example, at a film thickness of about 100 nm by vapor deposition or the like such that the film of the oxide covers cover the light emission end. In this case, at least a part of light emitted from the light emission end of the optical fiber 61*b* is absorbed by the metal film or the film of the oxide that covers the light emission end, and a photoacoustic wave is generated from the metal film or the film of the oxide.

Returning to FIG. 2, the ID detection circuit 60*c* comprises a memory that stores ID information (corresponding to identification information for identifying the device) of the photoacoustic wave light source unit 60, a reading circuit that reads the ID information from the memory, and the like. The ID detection circuit 60*c* outputs the ID information to the sub-controller 12 of the ultrasound diagnostic apparatus 10 when the photoacoustic wave light source unit 60 is connected to the connector 17 of the ultrasound diagnostic apparatus 10 or when the ultrasound diagnostic apparatus 10 is started after the connection of the photoacoustic wave light source unit 60. As a method of detecting that the photoacoustic wave light source unit 60 is connected to the ultrasound diagnostic apparatus 10, various kinds of known connection detection can be used. For example, an optical sensor, such as a photocoupler, may be provided or detection may be performed with an electrical or mechanical configuration.

The sub-controller 12 performs photoacoustic image measurement only in a case where the photoacoustic image mode is selected in the operating unit 15 and the ID information of the photoacoustic wave light source unit 60 is received. That is, the photoacoustic wave transmission timing signal is output from the synchronization signal generation unit 12*a*. Even though the photoacoustic image mode is selected in the operating unit 15, in a case where ID information different from the ID information of the photoacoustic wave light source unit 60 is received, the sub-controller 12 does not output the photoacoustic wave transmission timing signal.

Specifically, for example, in a case where the electrocardiograph unit 30, instead of the photoacoustic wave light source unit 60, is erroneously connected to the connector 17, since the ID information of the photoacoustic wave light source unit 60 is not received, the sub-controller 12 does not output the photoacoustic wave transmission timing signal. With this, it is possible to restrain failure in the electrocardiograph unit 30. In a case where the photoacoustic image mode is selected in the operating unit 15, and in a case where a device other than the photoacoustic wave light source unit 60 is connected to the connector 17, the sub-controller 12 outputs the effect to the main controller 11, and the main controller 11 makes the display unit 16 display a warning message or the like.

The failure detection circuit 60*d* confirms whether or not there is failure in the photoacoustic wave light source unit 60 when the photoacoustic wave light source unit 60 is connected to the connector 17 of the ultrasound diagnostic apparatus 10, when the ultrasound diagnostic apparatus 10 is started after the connection of the photoacoustic wave light source unit 60, or when the photoacoustic wave light source unit 60 operates. As detection of failure in the photoacoustic wave light source unit 60, for example, an abnormality of a current value or a voltage value of the light source unit 60*a* is detected. In a case where failure is detected by the failure detection circuit 60*d*, a detection signal is output to the main controller 11 through the sub-controller 12 of the ultrasound diagnostic apparatus 10, and the main controller 11 makes the display unit 16 displays the effect that failure is detected.

The ID detection circuit 60*c* and the failure detection circuit 60*d* in the photoacoustic wave light source unit 60 are subjected to digital control based on the clock signal generated in the clock signal generation unit 12*b* of the ultrasound diagnostic apparatus 10. In this way, the clock signal generation unit 12*b* of the ultrasound diagnostic apparatus 10 is used, whereby there is no need to provide a clock signal generation unit in the photoacoustic wave light source unit 60, and it is possible to achieve reduction in size.

Figure 6:
FIG. 6 is a timing chart of a photoacoustic image mode.

FIG. 6 is a timing chart showing the synchronization signal that is output from the synchronization signal generation unit 12*a*, a transmission timing of an ultrasonic wave based on the synchronization signal, a transmission timing of a photoacoustic wave, and a reception timing of the ultrasonic wave in the photoacoustic image mode. An ultrasonic wave transmission timing signal shown in FIG. 6 is a synchronization signal (corresponding to a first synchronization signal of the invention) that is output from the synchronization signal generation unit 12*a* to the transmission controller 13, a photoacoustic wave transmission timing signal is a synchronization signal (corresponding to a second synchronization signal of the invention) that is output from the synchronization signal generation unit 12a to the photoacoustic wave light source unit 60, and an ultrasonic wave reception timing signal is a synchronization signal (corresponding to a first synchronization signal of the invention) that is output from the synchronization signal generation unit 12a to the reception controller 14.

As shown in FIG. 6, the ultrasonic wave transmission timing signal and the ultrasonic wave reception timing signal are output at the same timing excluding when the photoacoustic wave transmission timing signal and the ultrasonic wave reception timing signal are output simultaneously, and the photoacoustic wave transmission timing signal is output between the ultrasonic wave transmission timing signals. The reception controller 14 starts reception of the reflected ultrasonic wave after a given delay time (for example, about 0.1 µs) from the timing at which the ultrasonic wave reception timing signal is received. Then, after the reflected ultrasonic wave is received in a given reception period, the reception controller 14 stops reception. The reception period can be set to a time (0.3 m×2/1540 m/s=0.39 ms; 1540 m/s is a sonic speed of an ultrasonic wave (10 MHz)) corresponding to a depth of about 30 cm, for example, taking a reverberation signal into consideration as well. Then, the reception controller 14 outputs a detection signal of the reflected ultrasonic wave to the main controller 11 along with the timing at which the ultrasonic wave reception timing signal is received.

The reception controller 14 starts reception of the photoacoustic wave immediately after the photoacoustic wave is transmitted from the photoacoustic wave generation unit 61c of the puncture needle 61 after the reception period of the reflected ultrasonic wave has elapsed. Then, the reception controller 14 stops reception after the photoacoustic wave is received in a given reception period. The reception period of the photoacoustic wave can be set to a time (0.3 m/1540 m/s=0.195 ms; 1540 m/s is a sonic speed of an ultrasonic wave (10 MHz)) corresponding to, for example, a depth of about 30 cm. The reception period of the photoacoustic wave becomes half the reception period of the reflected ultrasonic wave. Then, the reception controller 14 outputs a detection signal of the photoacoustic wave to the main controller 11 along with the timing at which the photoacoustic wave transmission timing signal is received. The image generation unit 11a of the main controller 11 generates an ultrasound image based on the input detection signal of the ultrasonic wave and generates a photoacoustic image based on the input detection signal of the photoacoustic wave. Then, the main controller 11 makes the display unit 16 display the ultrasound image on the photoacoustic image in a superimposed manner.

An interval between transmission of the ultrasonic wave and reception of the reflected ultrasonic wave, and transmission and reception of the photoacoustic wave may be set to one line interval. That is, detection of the reflected ultrasonic wave and detection of the photoacoustic wave may be performed alternately per line. In this case, since transmission and reception can be made to correspond on a one-to-one basis, it is possible to implement the configuration with inexpensive hardware.

Detection of the reflected ultrasonic wave and detection of the photoacoustic wave may be performed alternately per frame. Alternatively, detection of the reflected ultrasonic wave and detection of the photoacoustic wave may be performed alternately per a plurality of lines. Specifically, for example, in a case where one frame has 128 lines, detection of the reflected ultrasonic wave of the first to 64th lines may be performed, and then, detection of the photoacoustic wave of the first to 64th lines may be performed. Subsequently, detection of the reflected ultrasonic wave of the 65th to 128th lines may be performed, and then, detection of the photoacoustic wave of the 65th to 128th lines may be performed.

Figure 7:
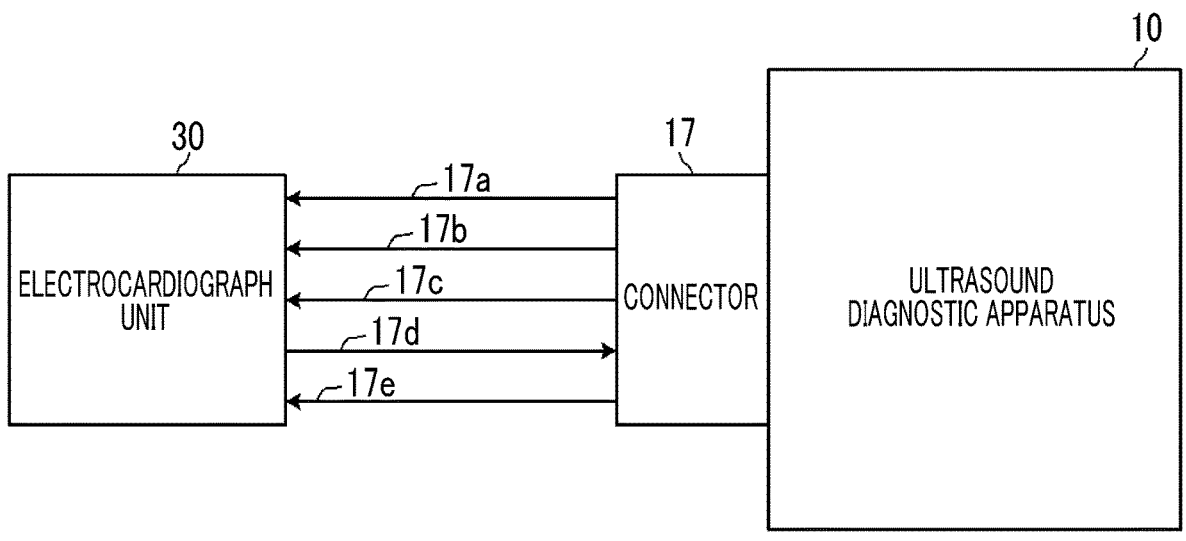
FIG. 7 is a diagram showing wirings of a connector of the first embodiment.
Figure 8:
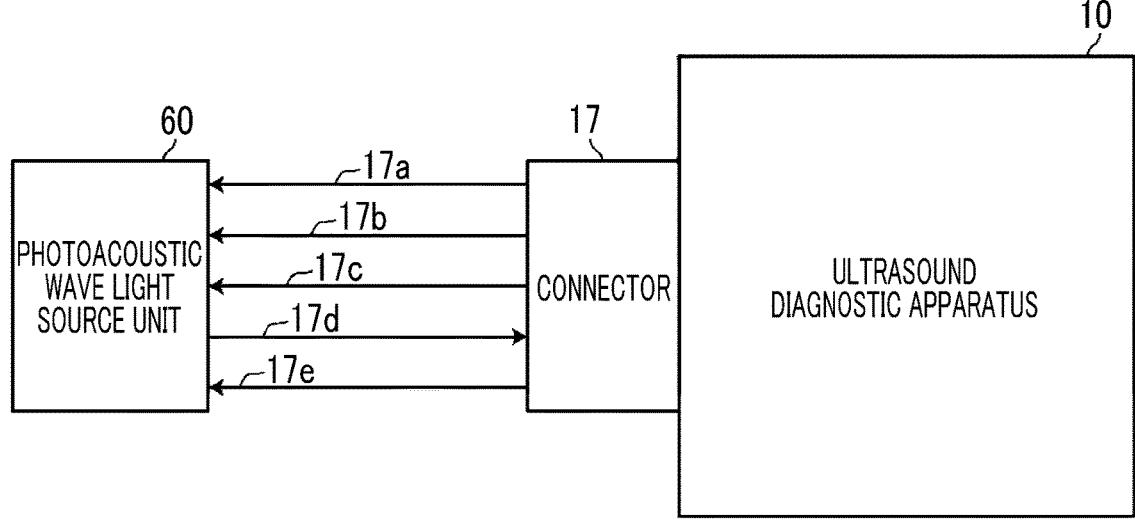
FIG. 8 is a diagram showing the wirings of the connector of the first embodiment.

Next, the connector 17 of the ultrasound diagnostic apparatus 10 will be described. FIG. 7 shows a state in which the electrocardiograph unit 30 is connected to the connector 17, and FIG. 8 shows a state in which the photoacoustic wave light source unit 60 is connected to the connector 17. The connector 17 of the embodiment has five wirings 17a to 17e as shown in FIGS. 7 and 8.

The first wiring 17a is a power line, and electric power is supplied from the ultrasound diagnostic apparatus 10 to the electrocardiograph unit 30 or the photoacoustic wave light source unit 60 through the first wiring 17a. The second wiring 17b is a clock signal line, and the clock signal is supplied from the ultrasound diagnostic apparatus 10 to the electrocardiograph unit 30 or the photoacoustic wave light source unit 60 through the second wiring 17b. The third wiring 17c is a synchronization signal line, and the synchronization signal is transmitted from the ultrasound diagnostic apparatus 10 to the electrocardiograph unit 30 or the photoacoustic wave light source unit 60 through the third wiring 17c.

The fourth wiring 17d is a data line, and the ECG signal, the ID information, and the failure detection signal output from the electrocardiograph unit 30 are input to the ultrasound diagnostic apparatus 10 through the fourth wiring 17d. Furthermore, the ID information and the failure detection signal output from the photoacoustic wave light source unit 60 are input to the ultrasound diagnostic apparatus 10 through the fourth wiring 17d. In FIGS. 7 and 8, although the fourth wiring 17d is shown by one line, it is preferable that the fourth wiring 17d has two or three lines to perform parallel transmission.

The fifth wiring 17e is a ground line, and a ground potential is supplied from the ultrasound diagnostic apparatus 10 to the electrocardiograph unit 30 or the photoacoustic wave light source unit 60 through the fifth wiring 17e.

With the ultrasound diagnostic system 1 of the first embodiment described above, a configuration is made in which the ultrasound probe 20 is controlled based on the synchronization signal generated by the synchronization signal generation unit 12a, the connector 17 having the synchronization signal line transmitting the synchronization signal generated by the synchronization signal generation unit 12a is provided, and the photoacoustic wave light source unit 60 is connectable to the connector 17. For this reason, it is possible to synchronize emission of light from the photoacoustic wave light source unit 60 and reception in the ultrasound probe 20 with high accuracy.

Furthermore, a configuration in which both of the electrocardiograph unit 30 and the photoacoustic wave light source unit 60 are connectable to the connector 17 is made. Accordingly, it is possible to reduce the space of the connector, and to achieve reduction in size. In addition, it is possible to restrain deterioration of electrical safety and electromagnetic compatibility (EMC) performance due to an increase in the number of connectors.

In the first embodiment described above, although the electrocardiograph unit 30 is connectable to the connector 17 of the ultrasound diagnostic apparatus 10, a configuration in which a phonocardiograph unit (corresponding to a pho- nocardiograph of the invention) may be connectable to the connector 17 of the ultrasound diagnostic apparatus 10 may be made. The phonocardiograph unit is configured by pro- viding a microphone for cardiac sound measurement instead of the electrode group 30a of the electrocardiograph unit 30.

There is no case where ECG detection and phonocardio- gram (PCG) detection, and photoacoustic image measure- ment (puncture) are simultaneously used clinically. For this reason, there are no problems in particular even though the electrocardiograph unit 30 and the phonocardiograph unit, and the photoacoustic wave light source unit 60 are con- nected to the connector 17 exclusively.

Figure 9:
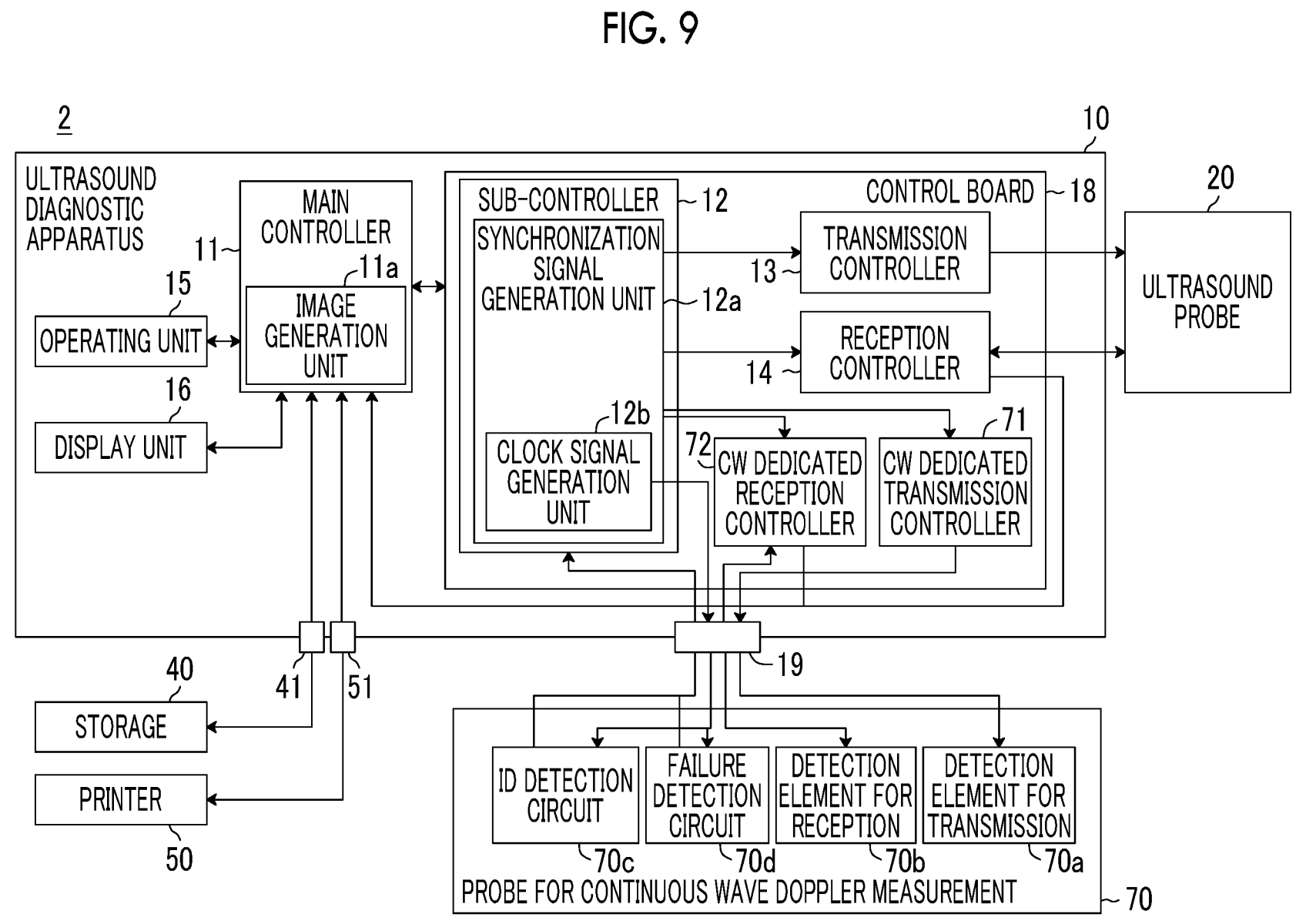
Figure 10:
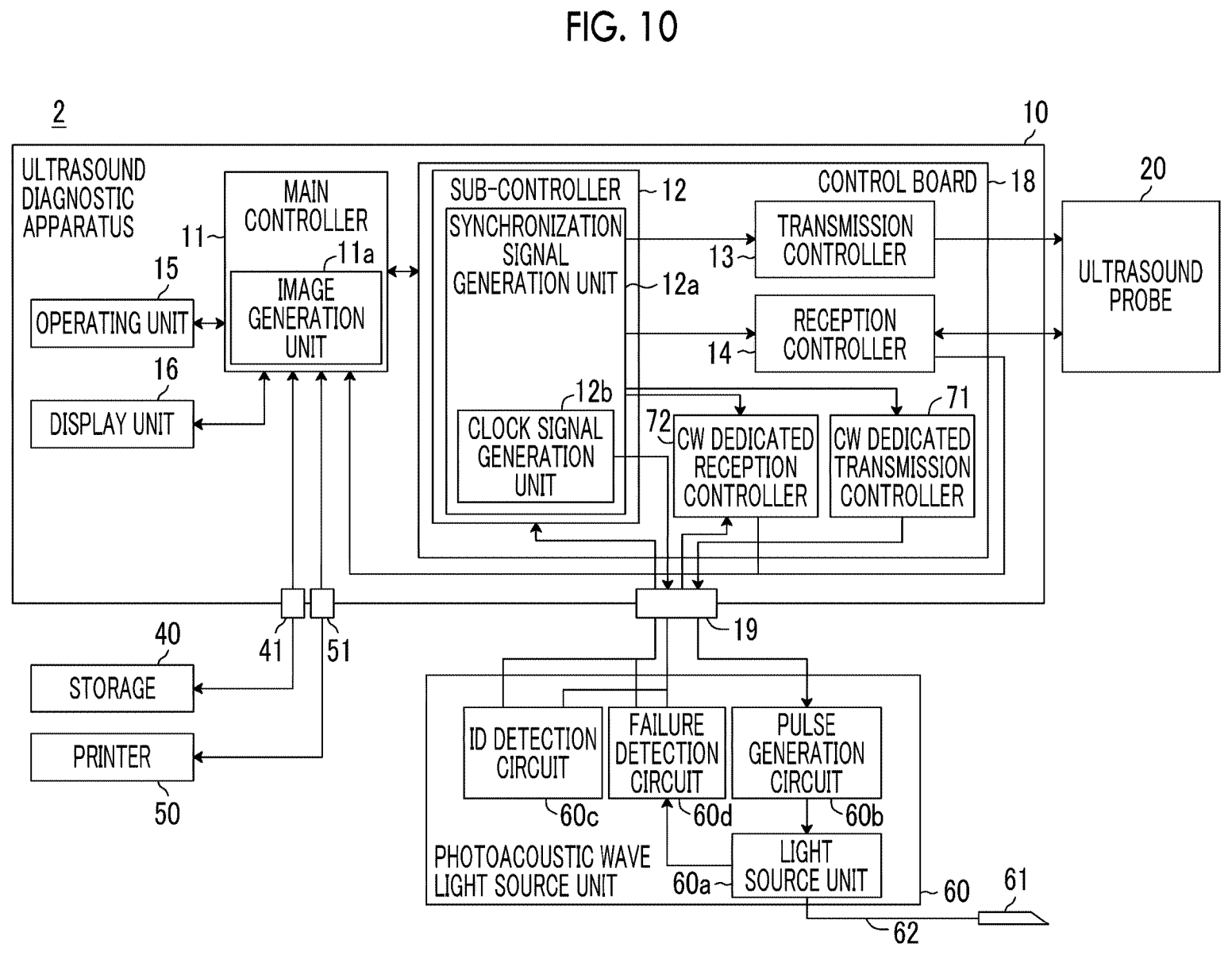

Next, an ultrasound diagnostic system using a second embodiment of an ultrasound diagnostic apparatus of the invention will be described. FIGS. 9 and 10 are block diagrams showing the schematic configuration of an ultra- sound diagnostic system 2 of the embodiment. The appear- ance of the ultrasound diagnostic system 2 of the embodi- ment is the same as the ultrasound diagnostic system 1 of the first embodiment shown in FIG. 3.

In the ultrasound diagnostic system 1 of the first embodi- ment described above, a configuration in which the electro- cardiograph unit 30 and the photoacoustic wave light source unit 60 are connectable to the connector 17 is made. The ultrasound diagnostic system 2 of the second embodiment comprises a connector 19 configured such that both of a probe 70 for continuous wave Doppler measurement and the photoacoustic wave light source unit 60 are connectable. FIG. 9 shows a state in which the probe 70 for continuous wave Doppler measurement is connected to the connector 19 of the ultrasound diagnostic apparatus 10. FIG. 10 shows a state in which the photoacoustic wave light source unit 60 is connected to the connector 19. The ultrasound diagnostic system 2 shown in FIG. 10 is the same as the ultrasound diagnostic system 1 shown in FIG. 9 except that, instead of the probe 70 for continuous wave Doppler measurement in the ultrasound diagnostic system 2 shown in FIG. 9, the photoacoustic wave light source unit 60 is connected to the connector 19.

First, the ultrasound diagnostic apparatus 10 in the ultra- sound diagnostic system 2 of the embodiment will be described. The ultrasound diagnostic apparatus 10 of the embodiment comprises a continuous wave (CW) dedicated transmission controller 71 and a CW dedicated reception controller 72 instead of the ECG processor 12c of the ultrasound diagnostic apparatus 10 of the first embodiment.

The CW dedicated transmission controller 71 generates a CW dedicated transmission signal based on the synchroni- zation signal output from the synchronization signal gen- eration unit 12a and transmits the CW dedicated transmis- sion signal to the probe 70 for continuous wave Doppler measurement through the connector 19. The probe 70 for continuous wave Doppler measurement makes an ultrasonic wave of continuous waves be transmitted from the detection element 70a for transmission to the subject in response to the CW dedicated transmission signal.

The CW dedicated reception controller 72 performs reception control of a reflected ultrasonic wave reflected from the subject with transmission of the ultrasonic wave of the continuous waves to the subject based on the synchro- nization signal output from the synchronization signal gen- eration unit 12a.

In a case where the probe 70 for continuous wave Doppler measurement is connected to the connector 19, the image generation unit 11a in the main controller 11 receives a detection signal output from a detection element 70b for reception of probe 70 for continuous wave Doppler mea- surement and generates a CW Doppler image based on the detection signal.

The CW dedicated transmission controller 71 and the CW dedicated reception controller 72 comprise an electric circuit that performs transmission and reception control described above, and the like.

As in the first embodiment, the sub-controller 12 controls transmission of the ultrasonic wave from the ultrasound probe 20 and reception of the reflected ultrasonic wave reflected from the subject with transmission of the ultrasonic wave to the subject. Furthermore, the sub-controller 12 controls transmission of the ultrasonic wave of the continu- ous waves from the probe 70 for continuous wave Doppler measurement described above and reception of the reflected ultrasonic wave reflected from the subject with transmission of the ultrasonic wave to the subject. In addition, as in the first embodiment, the sub-controller 12 controls emission of light from the photoacoustic wave light source unit 60.

The configurations of the synchronization signal genera- tion unit 12a and the clock signal generation unit 12b in the sub-controller 12 are the same as those in the first embodi- ment.

The operating unit 15 of the embodiment receives ON and OFF operations of a continuous wave Doppler measurement mode and ON and OFF operations of the photoacoustic image mode.

In a case where the ON operation of the continuous wave Doppler measurement mode is received in the operating unit 15, the synchronization signal generation unit 12a outputs a CW dedicated transmission timing signal and a CW dedi- cated reception timing signal described below based on a control schedule set in advance. In a case where the ON operation of the photoacoustic image mode is received in the operating unit 15, the synchronization signal generation unit 12a outputs a photoacoustic wave transmission timing sig- nal based on a control schedule set in advance.

Next, the probe 70 for continuous wave Doppler mea- surement will be described. The probe 70 for continuous wave Doppler measurement comprises the detection ele- ment 70a for transmission, the detection element 70b for reception, an ID detection circuit 70c, and a failure detection circuit 70d.

The detection element 70a for transmission is configured of a piezoelectric element or the like, and transmits the ultrasonic wave of the continuous waves to the subject. The detection element 70b for reception is also configured of a piezoelectric element or the like, and receives the reflected ultrasonic wave reflected from the subject with transmission of the ultrasonic wave of the continuous waves.

The ID detection circuit 70c comprises a memory that stores ID information of the probe 70 for continuous wave Doppler measurement, a reading circuit that reads the ID information from the memory, and the like. The ID detection circuit 70c outputs the ID information to the sub-controller 12 of the ultrasound diagnostic apparatus 10 when the probe 70 for continuous wave Doppler measurement is connected to the connector 19 of the ultrasound diagnostic apparatus 10 or when the ultrasound diagnostic apparatus 10 is started after the connection of the probe 70 for continuous wave Doppler measurement.

The sub-controller 12 performs continuous wave Doppler measurement only in a case where the ID information of the probe 70 for continuous wave Doppler measurement is received. As a method of detecting that the probe 70 for continuous wave Doppler measurement is connected to the ultrasound diagnostic apparatus 10, various kinds of known connection detection can be used. For example, an optical sensor, such as a photocoupler, may be provided or detection may be performed with a mechanical configuration.

The sub-controller 12 performs continuous wave Doppler measurement only in a case where the continuous wave Doppler measurement mode is selected in the operating unit 15 and the ID information of the probe 70 for continuous wave Doppler measurement is received. That is, the CW dedicated transmission timing signal and the CW dedicated reception timing signal are output from the synchronization signal generation unit 12a. Even though the continuous wave Doppler measurement mode is selected in the operating unit 15, in a case where ID information different from the ID information of the probe 70 for continuous wave Doppler measurement is received, the sub-controller 12 does not output the CW dedicated transmission timing signal and the CW dedicated reception timing signal.

Specifically, for example, in a case where the photoacoustic wave light source unit 60, instead of the probe 70 for continuous wave Doppler measurement, is erroneously connected to the connector 19, since the ID information of the probe 70 for continuous wave Doppler measurement is not received, the sub-controller 12 does not output the CW dedicated transmission timing signal and the CW dedicated reception timing signal. With this, it is possible to restrain failure in the photoacoustic wave light source unit 60 and erroneous emission of light from the photoacoustic wave light source unit 60. In a case where the continuous wave Doppler measurement mode is selected in the operating unit 15, and in a case where a device other than the probe 70 for continuous wave Doppler measurement is connected to the connector 19, the sub-controller 12 outputs the effect to the main controller 11, and the main controller 11 makes the display unit 16 display a warning message or the like.

The failure detection circuit 70d confirms whether or not there is failure in the probe 70 for continuous wave Doppler measurement when the probe 70 for continuous wave Doppler measurement is connected to the connector 19 of the ultrasound diagnostic apparatus 10, when the ultrasound diagnostic apparatus 10 is started after the connection of the probe 70 for continuous wave Doppler measurement, or when the probe 70 for continuous wave Doppler measurement operates. As detection of failure in the probe 70 for continuous wave Doppler measurement, for example, detection of short-circuit or open circuit of the wirings of the detection element 70a for transmission and the detection element 70b for reception, or the like is exemplified. In a case where failure is detected by the failure detection circuit 70d, a detection signal is output to the main controller 11 through the sub-controller 12 of the ultrasound diagnostic apparatus 10, and the main controller 11 makes the display unit 16 display the effect that failure is detected.

The ID detection circuit 70c and the failure detection circuit 70d in the probe 70 for continuous wave Doppler measurement are subjected to digital control based on the clock signal generated in the clock signal generation unit 12b of the ultrasound diagnostic apparatus 10. In this way, the clock signal generation unit 12b of the ultrasound diagnostic apparatus 10 is used, whereby there is no need to provide a clock signal generation unit in the probe 70 for continuous wave Doppler measurement, and it is possible to achieve reduction in size.

Figure 11:
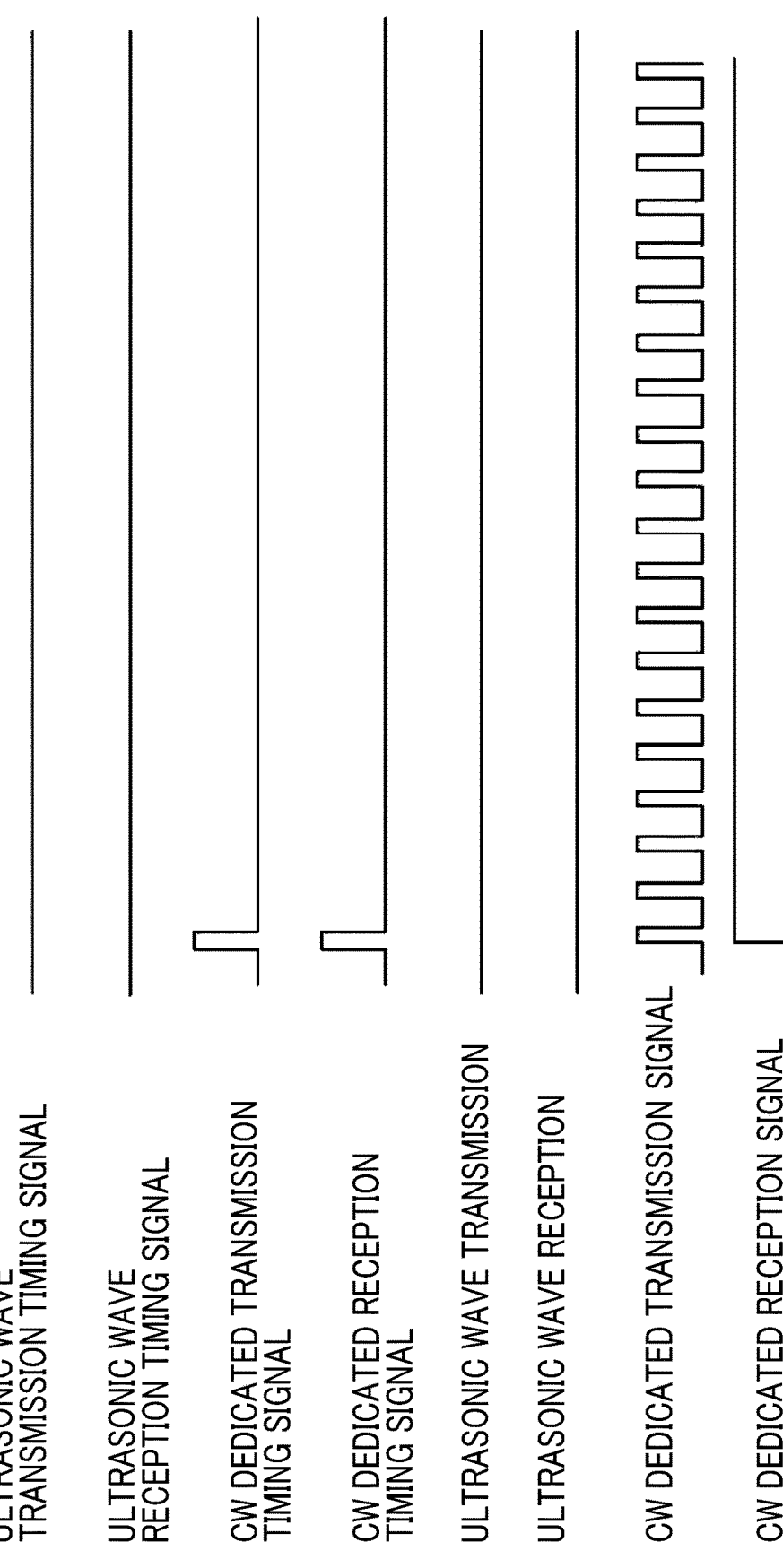
FIG. 11 is a timing chart of a continuous wave Doppler measurement mode.

FIG. 11 is a timing chart showing the synchronization signal that is output from the synchronization signal generation unit 12a, a transmission timing of the ultrasonic wave of the continuous waves based on the synchronization signal, and the reception timing of the ultrasonic wave.

Measurement of the ultrasound image in the ultrasound probe 20 and continuous wave Doppler measurement in the probe 70 for continuous wave Doppler measurement are not simultaneously performed, and only one of measurement of the ultrasound image and continuous wave Doppler measurement is performed. For this reason, in FIG. 11, the ultrasonic wave transmission timing signal and the ultrasonic wave reception timing signal remain zero.

The CW dedicated transmission timing signal shown in FIG. 11 is a synchronization signal (corresponding to a second synchronization signal of the invention) that is output from the synchronization signal generation unit 12a to the CW dedicated transmission controller 71, the CW dedicated reception timing signal is a synchronization signal (corresponding to a second synchronization signal of the invention) that is output from the synchronization signal generation unit 12a to the CW dedicated reception controller 72, the CW dedicated transmission signal is a control signal (corresponding to a signal generated based on a second synchronization signal of the invention) that is output from the CW dedicated transmission controller 71 to the detection element 70a for transmission, and a CW dedicated reception signal is a control signal (corresponding to a signal generated based on a second synchronization signal of the invention) that is output from the CW dedicated reception controller 72 to the detection element 70b for reception.

As shown in FIG. 11, the CW dedicated transmission timing signal and the CW dedicated reception timing signal are output at the same timing. The CW dedicated transmission controller 71 outputs the CW dedicated transmission signal having continuous pulse waves to the detection element 70a for transmission in response to the input CW dedicated transmission timing signal. The detection element 70a for transmission transmits the ultrasonic wave of the continuous waves to the subject in response to the input CW dedicated transmission signal.

The CW dedicated reception controller 72 outputs the CW dedicated reception signal to the detection element 70b for reception in response to the input CW dedicated reception timing signal. The detection element 70b for reception continuously performs reception of the ultrasonic wave in response to the CW dedicated reception signal. A detection signal detected by the detection element 70b for reception is received by the CW dedicated reception controller 72 and is then output to the main controller 11. Then, in the image generation unit Ila of the main controller 11, a continuous wave Doppler measurement image is generated based on the input detection signal and is displayed on the display unit 16.

Next, the operation in a case where the photoacoustic wave light source unit 60 is connected to the connector 19 of the ultrasound diagnostic apparatus 10 will be described. The configuration of the photoacoustic wave light source unit 60 itself is the same as that in the first embodiment described above.

In the embodiment, the control signal (corresponding to a signal generated based on a second synchronization signal of the invention) is output from the CW dedicated transmission controller 71 to the pulse generation circuit 60b in response to the synchronization signal output from the synchronization signal generation unit 12a, and the pulse generation circuit 60b generates a pulse signal based on the input control signal. Then, as in the first embodiment, the light source unit 60a emits pulsed light in response to the pulse signal output from the pulse generation circuit 60b. The CW dedicated transmission controller 71 outputs the control signal using monopolar transmission.

Even in the embodiment, the ON and OFF operations of the photoacoustic image mode are received by the operating unit 15. In a case where the ON operation of the photoacoustic image mode is received in the operating unit 15, the synchronization signal generation unit 12a outputs the synchronization signal based on a control schedule set in advance. In the photoacoustic image mode, as in the first embodiment, while ultrasound image measurement and photoacoustic image measurement are performed alternately, the synchronization signal that is output from the synchronization signal generation unit 12a, the transmission timing of the ultrasonic wave based on the synchronization signal, the transmission timing of the photoacoustic wave, and the reception timing of the ultrasonic wave are the same as those in the timing chart shown in FIG. 6. The operation of the ID detection circuit 70c and the failure detection circuit 70d in the photoacoustic wave light source unit 60 is the same as that in the above-described embodiment.

In a case where the ON operation of the photoacoustic image mode is received in the operating unit 15, continuous wave Doppler measurement is not performed.

Figure 12:
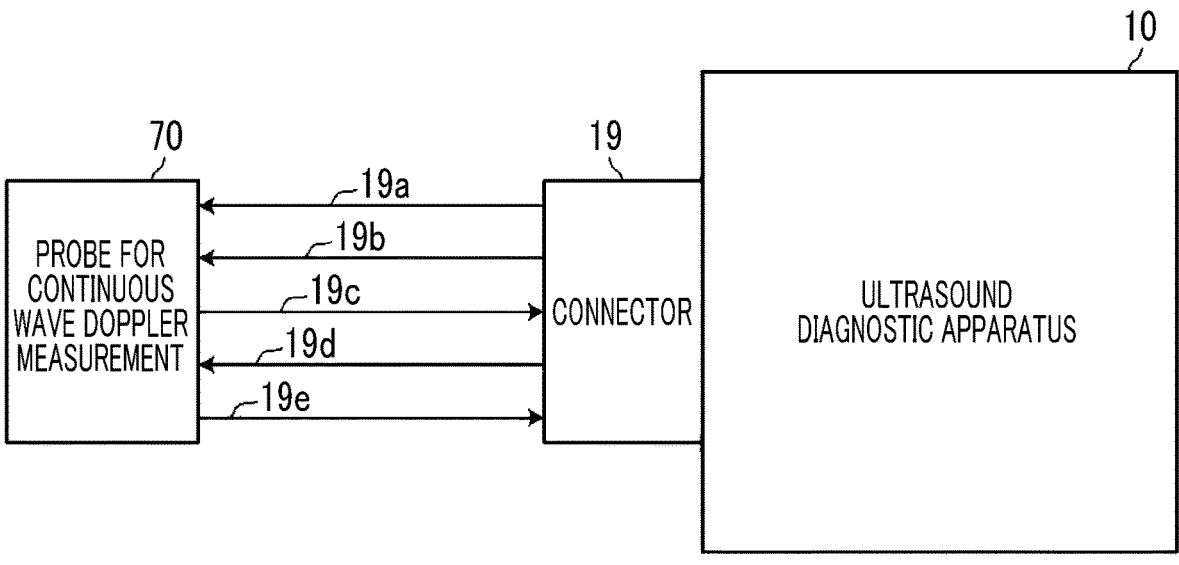
FIG. 12 is a diagram showing wirings of a connector of the second embodiment.
Figure 13:
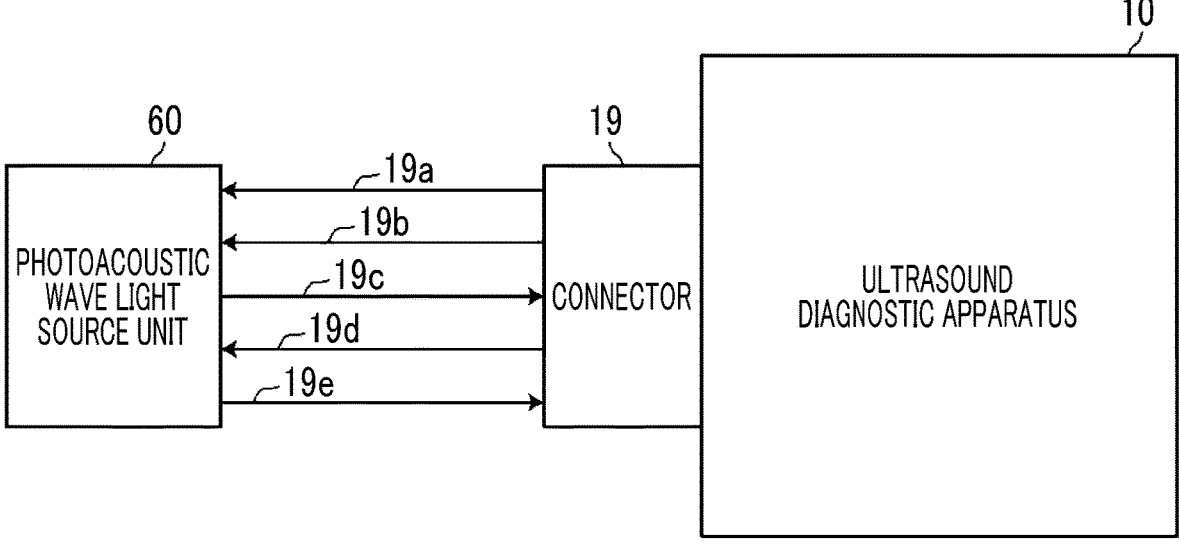
FIG. 13 is a diagram showing the wirings of the connector of the second embodiment.

Next, the connector 19 of the ultrasound diagnostic apparatus 10 will be described. FIG. 12 shows a state in which the probe 70 for continuous wave Doppler measurement is connected to the connector 19, and FIG. 13 shows a state in which the photoacoustic wave light source unit 60 is connected to the connector 19. The connector 19 of the embodiment has five wirings 19a to 19e as shown in FIGS. 12 and 13.

The first wiring 19a is a synchronization signal line (also referred to as a transmission signal line), and in the continuous wave Doppler measurement mode, the CW dedicated transmission signal is transmitted from the ultrasound diagnostic apparatus 10 to the detection element 70a for transmission through the first wiring 19a. In the photoacoustic image mode, the photoacoustic wave transmission timing signal is transmitted from the ultrasound diagnostic apparatus 10 to the pulse generation circuit 60b through the first wiring 19a.

The second wiring 19b is a clock signal line, and the clock signal is supplied from the ultrasound diagnostic apparatus 10 to the probe 70 for continuous wave Doppler measurement or the photoacoustic wave light source unit 60 through the second wiring 19b.

The third wiring 19c is a data line, and the ID information and the failure detection signal output from the probe 70 for continuous wave Doppler measurement are input to the ultrasound diagnostic apparatus 10 through the third wiring 19c. Furthermore, the ID information and the failure detection signal output from the photoacoustic wave light source unit 60 are input to the ultrasound diagnostic apparatus 10 through the third wiring 19c. In FIGS. 12 and 13, although the third wiring 19c is shown by one line, it is preferable that the third wiring 19c has two lines to perform parallel transmission.

The fourth wiring 19d is a ground line, and a ground potential is supplied from the ultrasound diagnostic apparatus 10 to the probe 70 for continuous wave Doppler measurement or the photoacoustic wave light source unit 60 through the fourth wiring 19d.

The fifth wiring 19e is a detection signal line (also referred to as a reception signal line), and the detection signal (also referred to as a reception signal) detected by the detection element 70b for reception of the probe 70 for continuous wave Doppler measurement is output to the CW dedicated reception controller 72 through the fifth wiring 19e.

With the ultrasound diagnostic system 2 of the second embodiment described above, a configuration is made in which the ultrasound probe 20 is controlled based on the synchronization signal generated by the synchronization signal generation unit 12a, the connector 19 having the synchronization signal line transmitting the synchronization signal generated by the synchronization signal generation unit 12a is provided, and both of the probe 70 for continuous wave Doppler measurement and the photoacoustic wave light source unit 60 are connectable to the connector 19. Accordingly, it is possible to reduce the space of the connector, and to achieve reduction in size. In addition, it is possible to restrain deterioration of electrical safety and EMC performance due to an increase in the number of connectors.

The probe 70 for continuous wave Doppler measurement is a device for circulatory diagnosis, and is not used simultaneously with the photoacoustic image (puncture) clinically. Accordingly, there are no problems in particular even though the probe 70 for continuous wave Doppler measurement and the photoacoustic wave light source unit 60 are connected to the connector 19 exclusively.

In the first and second embodiments described above, although a configuration in which two devices are connectable to one connector is made, three or more devices may be connectable to one connector. For example, a configuration in which the photoacoustic wave light source unit 60, the electrocardiograph unit 30, and the probe 70 for continuous wave Doppler measurement are connectable to one connector may be made.

In the first and second embodiments described above, although one connector is shared by two devices, the invention is not limited thereto, the connector 17 of the first embodiment or the connector 19 of the second embodiment may be a connector dedicated to the photoacoustic wave light source unit 60.

Figure 14:
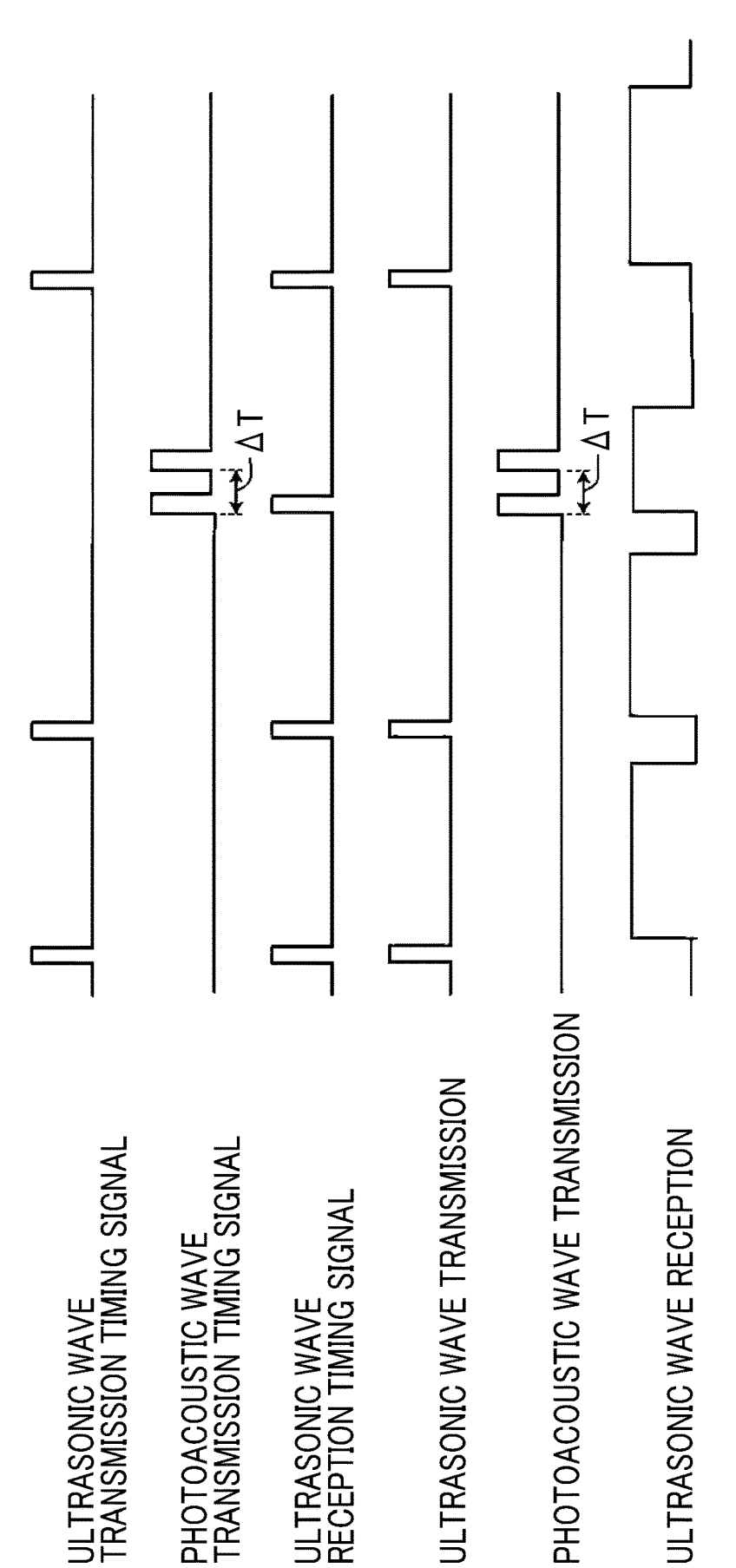
FIG. 14 is another timing chart of the photoacoustic image mode.
Figure 15:
FIG. 15 is a diagram showing an example of a photoacoustic image in a case where a photoacoustic wave is transmitted multiple times.

In the first and second embodiments described above, although, in the photoacoustic image mode, the photoacoustic wave is transmitted once at one ultrasonic wave reception interval (between the ultrasonic wave reception timing signals) as shown in FIG. 6, the invention is not limited thereto, and as shown in FIG. 14, a delay interval $\Delta T$ may be provided and the photoacoustic wave may be transmitted multiple times. In a case where the delay interval $\Delta T$ is set to, for example, 0.24 μs, 1540 m/s×0.24 μs=0.36 mm. Accordingly, in this case, as shown in FIG. 15, an image in which an image of the photoacoustic wave generation unit 61c at the distal end of the puncture needle 61 is arranged at two points at an interval of 0.36 mm in a depth direction is displayed. With this, it is possible to improve visibility of the distal end of the puncture needle 61.

There is a need to secure an interval during which the occurrence of an initial photoacoustic wave ends, and it is preferable that the delay interval $\Delta T$ is equal to or greater than 0.05 μs. The ultrasonic wave reception interval may be an interval during which a signal of one line is detected by the ultrasound probe 20 or may be an interval during which a signal of one frame is detected by the ultrasound probe 20.

Figure 16:
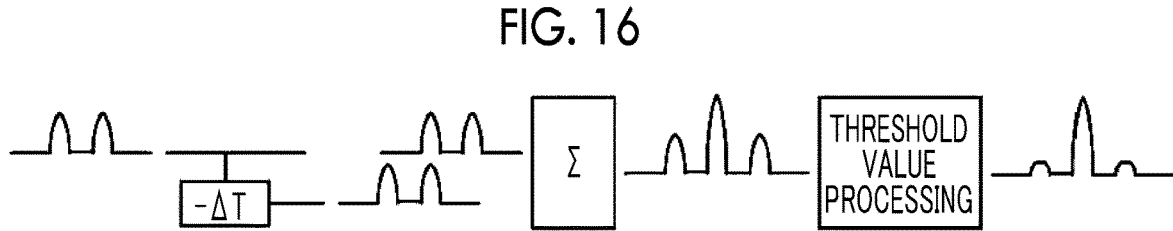
FIG. 16 is a diagram illustrating processing of a photoacoustic image detected by transmitting a photoacoustic wave multiple times.
Figure 17:
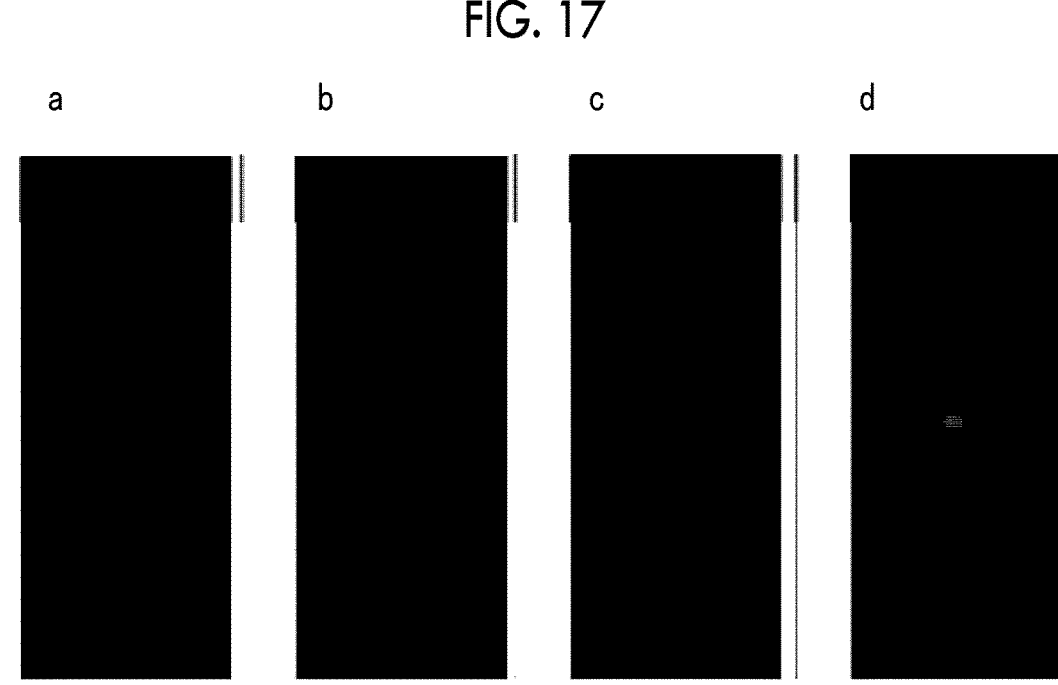
FIG. 17 is a diagram showing an example of a photoacoustic image generated through the processing shown in FIG. 16.

A photoacoustic image time-advanced by $\Delta T$ with respect to the photoacoustic image detected by providing the delay interval $\Delta T$ and transmitting the photoacoustic wave multiple times as described above, and the original photoacoustic image and the time-advanced photoacoustic image may be added to generate an added photoacoustic image. Then, threshold value processing may be executed on the added photoacoustic image using a threshold value that is about half a maximum value, making a signal equal to or less than the threshold value be equal to or less than half. FIG. 16 is a schematic view in which the above-described processing is arranged in time series. In FIG. 16, the processing progresses from left to right. A portion a of FIG. 17 shows a photoacoustic image detected with transmission of an initial photoacoustic wave, a portion b of FIG. 17 shows a photoacoustic image detected with transmission of a second photoacoustic wave, and a portion c of FIG. 17 shows a photoacoustic image time-advanced by ΔT. A portion d of FIG. 17 shows a photoacoustic image after the above-described threshold value processing is executed. With this, it is possible to more clearly display the distal end position of the puncture needle 61. In the embodiment, as shown in FIG. 14, since an initial photoacoustic wave transmission timing signal and the ultrasonic wave reception timing signal are the same timing, the photoacoustic image with transmission of the initial photoacoustic wave indicates the real distal end of the puncture needle 61.

The invention is not limited to the flow of the processing shown in FIG. 16, and correlation filtering processing may be executed to generate the same photoacoustic image as the photoacoustic image that is generated through the processing shown in FIG. 16.

In the first and second embodiments described above, although the ultrasound diagnostic apparatus 10 is portable, the invention is not limited to a portable ultrasound diagnostic apparatus, and may also be applied to a stationary ultrasound diagnostic apparatus.

In the first and second embodiments described above, although the puncture needle 61 is used as an embodiment of the insertion object of the invention, the invention is not limited thereto. The insertion object may be a needle for radiofrequency ablation that houses an electrode for use in radiofrequency ablation, a catheter that is inserted into a blood vessel, or a guide wire of the catheter that is inserted into the blood vessel. Alternatively, an optical fiber for laser treatment may be applied.

Although the invention has been described above based on the preferred embodiments, the insertion object and the photoacoustic measurement device of the invention are not limited only to the above-described embodiments, and various corrections and alterations in the configurations of the above-described embodiments are also included in the scope of the invention.

EXPLANATION OF REFERENCES

1, 2: ultrasound diagnostic system
10: ultrasound diagnostic apparatus
11: main controller
11*a*: image generation unit
12: sub-controller
12*a*: synchronization signal generation unit
12*b*: clock signal generation unit
12*c*: ECG processor
13: transmission controller
14: reception controller
15: operating unit
16: display unit
17: connector
17*a*: first wiring
17*b*: second wiring
17*c*: third wiring
17*d*: fourth wiring
17*e*: fifth wiring
18: control board
19: connector

19*a*: first wiring
19*b*: second wiring
19*c*: third wiring
19*d*: fourth wiring
19*e*: fifth wiring
20: ultrasound probe
30: electrocardiograph unit
30*a*: electrode group
30*b*: amplification circuit
30*c*: AD conversion circuit
30*d*: ID detection circuit
30*e*: failure detection circuit
40: storage
41, 51: USB connector
50: printer
60: photoacoustic wave light source unit
60*a*: light source unit
60*b*: pulse generation circuit
60*c*: ID detection circuit
60*d*: failure detection circuit
61: puncture needle
61*a*: puncture needle body
61*b*: optical fiber
61*c*: photoacoustic wave generation unit
61*d*: hollow portion
62: optical cable
70: probe for continuous wave Doppler measurement
70*a*: detection element for transmission
70*b*: detection element for reception
70*c*: ID detection circuit
70*d*: failure detection circuit
71: CW dedicated transmission controller
72: CW dedicated reception controller
ΔT: delay interval

What is claimed is:

1. An ultrasound diagnostic apparatus comprising:
a controller that has a first processor configured to function as a synchronization signal generation unit generating a first synchronization signal for controlling transmission and reception of an ultrasonic wave in an ultrasound probe, and controls the ultrasound probe based on the first synchronization signal;
a second processor configured to function as an ultrasound image generation unit that generates an ultrasound image based on a signal detected by the ultrasound probe; and
a connector that has a synchronization signal line transmitting a second synchronization signal generated in the synchronization signal generation unit and a data line transmitting data independently of the synchronization signal line, and outputs the second synchronization signal to the outside through the synchronization signal line,
wherein the connector is configured such that a light source device, which includes a laser diode or light-emitting diode, emitting light incident on an insertion object having a photoacoustic wave generator absorbing the light and generating a photoacoustic wave and an electrocardiograph that stores identification information are connectable in common,
wherein the controller is configured to output the second synchronization signal from the connector to the light source via the synchronization signal line if no identification information is obtained, and outputs the second synchronization signal corresponding to the electrocardiograph from the connector to the electrocardiograph via the synchronization signal line if the identification information indicating the electrocardiograph is obtained.

2. The ultrasound diagnostic apparatus according to claim 1,
wherein the light source device emits the light based on the second synchronization signal.

3. The ultrasound diagnostic apparatus according to claim 2,
wherein the synchronization signal generation unit has a clock signal generator generating a clock signal, and
the connector has a clock signal line transmitting the clock signal and outputs the clock signal to the outside through the clock signal line.

4. The ultrasound diagnostic apparatus according to claim 1,
wherein the synchronization signal generation unit has a clock signal generator generating a clock signal, and
the connector has a clock signal line transmitting the clock signal and outputs the clock signal to the outside through the clock signal line.

5. The ultrasound diagnostic apparatus according to claim 4,
wherein the second processor is configured to function as the ultrasound image generation unit which operates based on a clock signal different from the clock signal.

6. The ultrasound diagnostic apparatus according to claim 1,
wherein the synchronization signal generation unit generates the first synchronization signal and the second synchronization signal such that the light source device emits the light multiple times while a signal of one line is being detected by the ultrasound probe.

7. The ultrasound diagnostic apparatus according to claim 1,
wherein the synchronization signal generation unit generates the first synchronization signal and the second synchronization signal such that the light source device emits the light multiple times while a signal of one frame is being detected by the ultrasound probe.

8. The ultrasound diagnostic apparatus according to claim 1,
wherein the ultrasound diagnostic apparatus is portable.

9. The ultrasound diagnostic apparatus according to claim 1,
wherein the connector is further configured to output a signal generated based on the second synchronization signal to the outside through the synchronization signal line.

10. The ultrasound diagnostic apparatus according to claim 9,
wherein the connector is configured such that a probe for continuous wave Doppler measurement is connectable.

11. The ultrasound diagnostic apparatus according to claim 10,
wherein the signal generated based on the second synchronization signal is a continuous wave dedicated transmission signal and a continuous wave dedicated reception signal.

* * * * *